| United States Patent [19]
Blacklock et al.

[11] Patent Number: 4,510,083
[45] Date of Patent: Apr. 9, 1985

[54] PROCESS FOR PREPARING POLYPEPTIDES

[75] Inventors: Thomas J. Blacklock, Clark; Richard F. Shuman, Westfield, both of N.J.

[73] Assignee: Merck & Co., Inc., Rahway, N.J.

[21] Appl. No.: 499,743

[22] Filed: May 31, 1983

Related U.S. Application Data

[63] Continuation-in-part of Ser. No. 375,859, May 7, 1982, abandoned.

[51] Int. Cl.³ .......................................... C07C 103/52
[52] U.S. Cl. ............................................. 260/112.5 R
[58] Field of Search ................................ 260/112.5 R

[56] References Cited

U.S. PATENT DOCUMENTS 3,846,398 11/1974 Hirschmann et al. ....... 260/112.5 R
3,846,399 11/1974 Hirschmann et al. ....... 260/112.5 R
3,923,772 12/1975 Otsuka et al. ................ 260/112.5 R
3,951,741 4/1976 Pfaender et al. .............. 260/112.5 R
4,256,632 3/1981 Levin et al. ................... 260/112.5 R
4,267,344 5/1981 Halstrom et al. ............. 260/112.5 R

OTHER PUBLICATIONS

Hirschmann et al., *J. Org. Chem.*, 32, 3415–25, (1967).
Kircher, *Liebigs Amin. Chem.*, 275–284, (1980).
Iwakura et al., *Biopolymers*, 9, 1419–27, (1970).
Denkewalter et al., *J. Am. Chem. Soc.*, 88, 3163, (1966).

*Primary Examiner*—Delbert R. Phillips
*Assistant Examiner*—F. T. Moezie
*Attorney, Agent, or Firm*—Salvatore C. Mitri; Michael C. Sudol; Mario A. Monaco

[57] ABSTRACT

A process for producing polypeptides is disclosed wherein potassium, rubidium, or cesium serves as the counterion for both the carbonate buffer system and the amino acid or peptide salts employed.

4 Claims, No Drawings

PROCESS FOR PREPARING POLYPEPTIDES

BACKGROUND OF THE INVENTION

This application is a continuation-in-part of Ser. No. 375,859 filed May 7, 1982, now abandoned.

Two basic methods are described in the literature in which an amino acid N-carboxyanhydride (NCA) is coupled with either another amino acid or a peptide in an aqueous medium to produce a dipeptide or a polypeptide.

One method [Hirschmann, et al., *J. Org. Chem.*, 32, 3415–3425 (1967) and Kircher, et al., *Liebigs Ann Chem*, 275–284 (1980)] involves rapidly adding a solid NCA to an aqueous mixture of an appropriate amino acid or peptide salt, the mixture being buffered with a 5–10 fold molar excess of potassium borate, or sodium borate to a pH of 10.2. During the reaction and until coupling is completed, the reaction mixture is maintained at pH 10.2 by the continuous addition of alkali. Essentially the same method is disclosed in U.S. Pat. No. 3,846,399 except that the pH of the reaction mixture is maintained between 4–11, preferably between 8–10.5.

This method is not commercially attractive since it requires the use of a solid NCA, continuous pH adjustment, and a pH adjustment prior to product isolation which affords insoluble borate salts. These salts are either difficult and time consuming to remove by filtration or require extreme dilution with water before a tractable solution of the product can be obtained.

The other method [Katakai, et al., *Biopolymers*, 9, 1419–1427 (1970)] involves dissolving an NCA in acetonitrile and the resulting solution is then added to a two-phase acetonitrile-water mixture containing 0.1 mole of an appropriate amino acid or peptide. The mixture is buffered with one equivalent of sodium carbonate and cooled to −15° C.

This method is also not commercially attractive since effective concentrations are limited to about 0.1 molar. This procedure also results in solubility problems (crystallization of reagents) which prevent complete reaction and produce lower yields. In addition, freezing of the aqueous layer at the temperatures specified can make stirring the reaction mixture difficult.

U.S. Pat. No. 3,846,398 discloses a different method for obtaining polypeptides in which N-thiocarboxy amino acid anhydride (NTA), or derivatives thereof are employed with borate and phosphate buffers. Although intermediates need not be isolated in the latter NTA process, it is lengthy and involves several steps since it requires both dethiocarboxylation and the use and removal of protecting groups on the NTA, the amino acids, and the peptide products.

SUMMARY OF THE INVENTION

It has now been surprisingly found that when either potassium carbonate, rubidium carbonate, or cesium carbonate is employed in the process of the invention to produce polypeptides, the coupling reaction can be run at significantly higher concentrations of reactants and at lower temperatures while retaining complete reactant solubility and obtaining higher, commercially acceptable product yields. These alkali metal carbonates buffer the reaction system and provide the appropriate counterion for the amino acid(s) or peptide(s) employed.

The results obtained by employing either potassium, rubidium or cesium as the counterion were unexpected since one would anticipate that either lithium and/or sodium would be more effective as counterions because they are both higher in the Periodic Chart (Group Ia). As shown hereinafter, however, the alkali metal counterions of the invention are more effective than either lithium or sodium. Since potassium carbonate is less expensive and is more readily available commercially than either rubidium or cesium carbonate, it is preferred.

The polypeptides obtained are known and can be used to prepare pharmaceutical compounds such as, for example, antihypertensives, diuretics, gastric acid inhibitors, and the like.

In general, the process of the invention involves rapidly adding a solution of an amino acid N-carboxyanhydride (NCA) to a solvent system at reduced temperature. Said solvent system contains either another amino acid salt or a peptide salt containing the alkali metal counterion of the invention as well as the corresponding carbonate. This reaction mixture is then stirred until the reaction is complete (determined by high pressure liquid chromatography (HPLC) monitoring) following which the coupled reaction product is recovered by standard techniques such as, for example, phase separation, crystallization, and the like.

Thus, the process of the invention readily enables one to obtain a desired polypeptide through a series of sequential reactions. That is, the process of the invention can be employed to obtain initially a dipeptide which can then be further reacted to obtain a tripeptide. In like manner, the tripeptide thus produced can be coupled to another peptide or amino acid to obtain a tetrapeptide, and so on.

In the process of the invention, the molar excess of an amino acid NCA or of a peptide (or another amino acid) need not be more than about 5%.

The solvent system employed can consist of only water or it can be a co-solvent system comprising water and, as a co-solvent, an aprotic organic solvent such as, for example, acetonitrile ($CH_3CN$), tetrahydrofuran (THF), ethyl acetate (EtOAc), dimethylformamide (DMF), and the like. When a co-solvent system is employed, the ratio of aprotic organic solvent:water (v/v) can generally be about 1:1.

The molar concentration of peptide (or amino acid) salt in the buffered solvent system should be about 0.01–1.0M, preferably about 0.25–0.75M.

The time of addition of the amino acid NCA-containing solution to the solvent system containing the desired peptide or amino acid should be within about 10 minutes, preferably within about 5 minutes or less.

The temperature at which the invention process reaction can be run can be about −10° C. to 10° C., preferably about −5° to 5° C.

The molar ratio of alkali metal carbonate to peptide (or amino acid) that can be employed is generally about 1 to 1. Amounts of either alkali metal carbonate and/or peptide (or amino acid) outside this range can be employed, but do not result in improving the product yield or the process of the invention and may, in fact, decrease product yield.

The initial pH of solvent system in which the coupling reaction occurs generally reaches about 10–13.

The amino acids or peptides that can be employed to produce polypeptides according to the process of the invention include, but are not limited to, alanine, arginine, asparagine, aspartic acid, cysteine, cystine, glutamic acid, glutamine, glycine, histidine, isoleucine, leucine, lysine, methionine, ornithine, phenylalanine, proline, serine, threonine, tryptophan, tyrosine, valine, and the like, as well as admixtures and combinations thereof.

Where desired or as required, these amino acids or peptides can be protected with appropriate protecting groups during the reaction and then deprotected to obtain the final product. The nature and type of protecting groups that can be used, their application, and their subsequent removal are well documented in the literature and known to those skilled in the art.

The following examples are provided to further illustrate the best mode currently known for carrying out the process of the invention.

EXAMPLE 1

A two-phase mixture of water (500 ml), proline (31.5 g, 0.274 m), potassium hydroxide (15.6 g (corrected for $H_2O$ and $K_2CO_3$ content), 0.274 m), potassium carbonate (36.1 g, 0.261 m), and acetonitrile (500 ml) was prepared and cooled to 0° C. A solution of alanine-N-carboxyanhydride (alanine NCA) (30.0 g, 0.261 m) in sieve-dried (K.F., 0.1%) acetonitrile (40 ml) was prepared and cooled to 10°–15° C. This solution was rapidly added to the stirred, two-phase mixture during which time the temperature of this reaction mixture rose to 5° C. The reaction mixture was stirred until the reaction was complete as determined by HPLC while its temperature was maintained at about 0° to 5° C. The temperature of the reaction mixture was then raised to 10° C., stirring was discontinued, and the layers that formed were permitted to separate. The aqueous phase (pH 9.4–10.2) was removed, weighed, and assayed against an external standard by high pressure liquid chromatography (HPLC) for alanylproline content. Found: 43.9 g; 90.3% yield.

EXAMPLES 2–22

Following the procedures described in Example 1 above, additional alanine-proline dipeptides were obtained. The ingredients, systems and processing conditions employed as well as the results obtained are set forth in Table I below:

TABLE I

| Example No. | Solvent System | NCA[a] (Moles) | Base | Counterion Buffer | Reaction Mixture Molar Ratio NCA/Pro/Base/Buffer | Temp. Range (°C.) | % Yield AlaPro (HPLC) |
|---|---|---|---|---|---|---|---|
| 2 | $CH_3CN/H_2O$ | 0.522 | KOH | $K_2CO_3$ | 1/1/1/1 | −18 to −16[b] | 65.0 |
| 3 | $CH_3CN/H_2O$ | 0.261 | KOH | $K_2CO_3$ | 1/1/1/1 | −15 to −13[b] | 64.8 |
| 4 | $CH_3CN/H_2O$ | 0.261 | KOH | $K_2CO_3$ | 1/1/1/1 | −10 to −4 | 91.8 |
| 5 | $CH_3CN/H_2O$ | 0.261 | NaOH | $Na_2CO_3$ | 1/1/1/1 | −10 to −4 | 78.4 |
| 6 | $CH_3CN/H_2O$ | 0.100 | KOH | $K_2CO_3$ | 1/1.05/1/1 | 0 to 1 | 96.1 |
| 7 | $CH_3CN/H_2O$ | 0.100 | NaOH | $Na_2CO_3$ | 1/1.05/1/1 | 0 to 2 | 90.2 |
| 8 | $CH_3CN/H_2O$ | 0.261 | LiOH | $Li_2CO_3$ | 1/1.05/1.05/1 | 0 to 5[c] | 80.4 |
| [d]9 | $CH_3CN/H_2O$ | 0.248 | KOH | $H_3BO_3$[e] | 1/1.05/1.05/1.05 | 0 to 4 | 92.3 |
| [d]10 | $CH_3CN/H_2O$ | 0.248 | KOH | $H_3BO_3$[e] | 1/1.05/1.05/5.30 | 0 to 5 | 93.8 |
| 11 | $CH_3CN/H_2O$ | 0.261 | NaOH | $Na_2CO_3$ | 1/1.02/1/1 | −5 to −2 | 78.2 |
| 12 | $CH_3CN/H_2O$ | 0.261 | KOH | $K_2CO_3$ | 1/1.02/1/1 | −5 to 0 | 90.5 |
| 13 | $CH_3CN/H_2O$ | 0.261 | RbOH | $Rb_2CO_3$ | 1/1.02/1/1 | −5 to 0 | 90.8 |
| 14 | $CH_3CN/H_2O$ | 0.261 | CsOH | $Cs_2CO_3$ | 1/1.02/1/1 | −5 to 0 | 93.3 |
| 15 | $CH_3CN/H_2O$ | 0.261 | KOH | $K_2CO_3$ | 1/2.10/2.10/1 | 0 to 6 | 92.6 |
| 16 | $CH_3CN/H_2O$ | 0.261 | KOH | None | 1/1.05/1.05/0 | 0 to 5 | 74.5 |
| 17 | $CH_3CN/H_2O$ | 0.261 | KOH | $K_2CO_3$ | 1/1.05/1.05/2.0 | 0 to 6 | 91.6 |
| 18 | $CH_3CN/H_2O$ | 0.261 | KOH | $K_2CO_3$ | 1/1.05/1.05/1 | 0 to 4 | 91.6 |
| [f]19 | $CH_3CN/H_2O$ | 0.261 | KOH | $K_2CO_3$ | 1/1.05/1.05/1 | 0 to 6 | 75.5 |
| 20 | $THF/H_2O$ | 0.261 | KOH | $K_2CO_3$ | 1/1.05/1.05/1 | 0 to 6 | 88.9 |
| 21 | $EtOAc/H_2O$ | 0.261 | KOH | $K_2CO_3$ | 1/1.05/1.05/1 | 0 to 6 | 86.6 |
| [g]22 | $H_2O$ | 0.261 | KOH | $K_2CO_3$ | 1/1.05/1.05/1 | 0 to 9 | 94.0 |

[a]NCA dissolved separately in the organic solvent unless noted otherwise.
[b]Reaction temperature too cold and caused some of the reactants to precipitate.
[c]Some solids ($Li_2CO_3$) present prior to and throughout reaction which could not be separated from product.
[d]pH of reaction mixture and final product was 11.3–11.6; in all other reaction mixtures, pH was 12.0–13.0 and pH of final products was 9.0–10.0. Isolation of product was achieved only after extreme dilution with water.
[e]Potassium salts of boric acid were prepared in situ by partial neutralization with potassium hydroxide.
[f]Ratio (v/v) of $CH_3CN/H_2O$ was 3:1.
[g]NCA dissolved separately in a minimum amount of $CH_3CN$ or THF.

As the results in Table I reveal, the alkali metal counterions of the invention consistently resulted in significantly higher yields of dipeptide (Examples 4, 6, 12–15 and 17) than those obtained when either lithium or sodium carbonate was employed (Examples 5, 8 and 11), all other reaction conditions being held substantially constant. In addition, these higher yields were obtained regardless of the solvent system employed, as shown in Examples 20 and 21, as well as when water was the sole solvent (Example 22). When the ratio of co-solvent: water was increased above about 1:1 (i.e., 3:1 in Example 19), however, the yield was not satisfactory. Furthermore, even when the level of NCA was reduced, high yield was obtained employing an alkali counterion of the invention (Example 6) as compared to employing sodium as the counterion at the same NCA level (Example 7). In Examples 9 and 10, when a borate was employed as the buffer, the product was difficult to isolate despite the relatively high yields obtained. Example 16 illustrates that when no buffer was employed, product yield was significantly lowered. When lithium carbonate was employed as the buffer (Example 8), undersireable solids were present throughout the reaction which could not be separated from product.

As mentioned earlier, the process of the invention can be readily employed to produce various combinations of polypeptides such as, for example, valylserine, leucylvaline, alanylleucine, phenylalanylleucine, glycylphenylalanine, tyrosylserine, alanylserine, tryptophanylleucine, prolylphenylalanine, isoleucyllysine, phenylalanylarginine, methionyltyrosine, alanylphenylalanine, isoleucyltryptophan, valylhistidine, leucylphenylalanine, and the like.

What is claimed:

1. A process for sequentially producing polypeptides comprising:
   (a) preparing a solvent system containing an amino acid or a peptide and an alkali metal carbonate, said alkali metal being selected from the group consisting of potassium, rubidium, and cesium; said amino acid or peptide being selected from the group consisting of alanine, arginine, asparagine, aspartic acid, cysteine, cystine, glutamic acid, glutamine, glycine, histidine, isoleucine, leucine, lysine, methionine, ornithine, phenylalanine, proline, serine, threonine, tyrptophan, tyrosine, valine, and admixtures and combinations thereof; and, said solvent system comprises only water or water and an aprotic organic co-solvent selected from the group consisting of acetonitrile, tetrahydrofuran, ethyl acetate, dimethylformamide, or combinations thereof;
   (b) maintaining the temperature of said solvent system at about $-10°$ to $10°$ C.;
   (c) rapidly adding to said solvent system a solution of an amino acid N-carboxyanhydride (NCA) to form a reaction mixture, said amino acid being selected from those defined in (a) above and the excess molar concentration of said NCA, peptide, or amino acid in said reaction mixture being less than about 5%;
   (d) stirring said reaction mixture for no more than about 10 minutes or until the reaction is complete; and,
   (e) recovering the coupled reaction polypeptide product from said reaction mixture.

2. The process of claim 1 wherein the molar concentration of said peptide or amino acid is about 0.01–1.0M.

3. The process of claim 1 wherein the temperature of said solvent system is about $-5°$ to $5°$ C.

4. The process of claim 1 wherein said alkali metal carbonate is potassium carbonate.

* * * * *